(12) United States Patent  (10) Patent No.: US 8,308,348 B2
Boehm et al.                (45) Date of Patent:     Nov. 13, 2012

(54) DEVICE FOR DETERMINING THE DEW-POINT TEMPERATURE OF A TEST GAS

(75) Inventors: Alfred Boehm, Viechtach (DE); Wilhelm Binder, Tiefenbach (DE)

(73) Assignee: Bartec Benke GmbH, Reinbek/Hamburg (DE)

( * ) Notice: Subject to any disclaimer, the term of this patent is extended or adjusted under 35 U.S.C. 154(b) by 1011 days.

(21) Appl. No.: 11/659,207

(22) PCT Filed: Jul. 28, 2005

(86) PCT No.: PCT/EP2005/008219
§ 371 (c)(1),
(2), (4) Date: Aug. 10, 2009

(87) PCT Pub. No.: WO2006/015734
PCT Pub. Date: Feb. 16, 2006

(65) Prior Publication Data
US 2009/0296771 A1    Dec. 3, 2009

(30) Foreign Application Priority Data
Aug. 6, 2004 (DE) .......................... 10 2004 038 397

(51) Int. Cl.
G01N 25/02 (2006.01)
G01J 5/00 (2006.01)
G01K 1/16 (2006.01)
G01K 11/00 (2006.01)
(52) U.S. Cl. ............ 374/28; 374/161; 374/120; 374/130
(58) Field of Classification Search .................... 371/28, 371/161, 130, 120
See application file for complete search history.

(56) References Cited

U.S. PATENT DOCUMENTS

| 3,528,278 A * | 9/1970 | Sterling ........................... 374/19 |
| 3,856,404 A | 12/1974 | Hershler |
| 4,946,288 A * | 8/1990 | Siska et al. ..................... 374/20 |
| 5,022,045 A * | 6/1991 | Elliott ............................. 374/20 |
| 5,088,833 A * | 2/1992 | Tsang et al. .................... 374/17 |
| 5,396,325 A | 3/1995 | Carome et al. |
| 5,482,371 A * | 1/1996 | Nishizawa et al. ............. 374/20 |
| 5,971,609 A * | 10/1999 | Kijima et al. ................... 374/17 |
| 2004/0008749 A1 * | 1/2004 | Tsang et al. .................... 374/16 |
| 2004/0042526 A1 * | 3/2004 | Zlochin ........................... 374/16 |

(Continued)

FOREIGN PATENT DOCUMENTS
DE       3543155 CZ       6/1986
(Continued)

OTHER PUBLICATIONS

"Thermal Conductivity of some common Materials and Gases" from the Engineering Toolbox cited by the Examiner (no. date).*

(Continued)

Primary Examiner — Mirellys Jagan
(74) Attorney, Agent, or Firm — Jacobson Holman PLLC

(57) ABSTRACT

The invention relates to a device for determining the dew point temperature of a measurement gas, having a light guide, a condensation surface located on the light guide and whose reflectivity is dependent on the condensation of the measurement gas, a light source for emitting light through the light guide onto the condensation surface, a light sensor for determining the light intensity reflected back into the light guide by the condensation surface and means for adjusting the temperature of the condensation surface, which has a semihydrophobic construction.

19 Claims, 5 Drawing Sheets

U.S. PATENT DOCUMENTS

| | | | |
|---|---|---|---|
| 2004/0240515 A1* | 12/2004 | Egan et al. .................... | 374/120 |
| 2006/0083287 A1* | 4/2006 | Derevyagin et al. ............ | 374/28 |
| 2007/0171955 A1* | 7/2007 | Kanai et al. .................... | 374/28 |

FOREIGN PATENT DOCUMENTS

| | | |
|---|---|---|
| DE | 1970853 A1 | 2/1997 |
| DE | 20012060 U1 | 7/1999 |
| DE | 19915095 A1 | 12/1999 |
| DE | 10056771 A1 | 3/2000 |
| EP | 0843174 A1 | 5/1998 |

OTHER PUBLICATIONS

Lance D. Eske, et al.; "Character of SiO$_2$ surface using AFM, contact angles and a novel dewpoint technique"; Elsevier Science B.V.; Colloids and Surfaces A: Physicochemical and Engineering Aspects 154; 1999; pp. 33-51.

Shigeaki Matsumoto; "The measurement of tiny dew droplets at the initial deposition stage and dew point using a phase-shift interference microscope"; Institute of Physics Publishing, Measurement Science and Technology; Oct. 14, 2003pp. 2075-2080.

\* cited by examiner

US 8,308,348 B2

DEVICE FOR DETERMINING THE DEW-POINT TEMPERATURE OF A TEST GAS

This is a nationalization of PCT/EP2005/008219 filed 28 Jul. 2005 and published in German.

BACKGROUND OF THE INVENTION (1) Field of the Invention

The invention relates to a device for determining the dew point temperature of a measurement gas, having a light guide, a condensation surface located on the light guide and whose reflectivity is dependent on the condensation of the measurement gas, a light source for emitting light through the light guide onto the condensation surface, a light sensor for determining the light intensity reflected back into the light guide by the condensation surface and means for adjusting the temperature of the condensation surface, according to the preamble of claim 1.

(2) Description of Related Art Including Information Disclosed under 37 CFR 1.97 and 1.98

Dew point sensors and methods for determining the dew point temperature of a measurement gas are known. These sensors and methods are based on the principle that as a function of its temperature a gas is in a position to solely absorb a certain water vapour quantity, which rises with increasing temperature.

If a water vapour-containing gas is cooled to below the so-called dew point temperature, excess water vapour is precipitated and condensation occurs. This condensation effect can be utilized metrologically.

Thus, e.g. DE 199 15 095 A1 discloses a so-called dew point mirror hygrometer, which has a dew point mirror on which shines a light source and which is in contact with the measurement gas. The light reflected and/or scattered by the dew point mirror is detected by a photoreceiver. If as a result of a change in the dew point mirror temperature the measurement gas dew point temperature is reached, condensate is deposited on said mirror. At this time there is a change to the reflectivity and/or diffusing power of the dew point mirror and consequently the light intensity detected by the photoreceiver also changes.

In the case of the device known from DE 199 15 095 A1 the light is passed from the light source to the dew point mirror and from there to the photoreceiver directly through the measurement gas. In this case, the measurement signal at the photoreceiver can be falsified by any impurities, water droplets and/or ice crystals present in the measurement gas and which also absorb and/or scatter light. In addition, any impurities present in the measurement gas can be deposited on the dew point mirror surface, which can also falsify the measurement signal.

Another device for determining the dew point temperature is described in DE 200 12 060 U1. In said device the light path runs from the light source to the light sensor essentially through a medium differing from the measurement gas. This largely prevents an undesired absorption and/or scattering of the light through the measurement gas and also an undesired contamination of the light path. According to the teaching of DE 200 12 060 U1 the light is passed through a light guide to condensation areas located on the light guide surface and which are in contact with the measurement gas. If a condensate is deposited in the condensation areas, there is a change there to the critical angle for the total reflection of the light. This can lead to a coupling or feeding out of light and this can be detected at the light sensor as a change to the light intensity.

To concentrate the condensation of the measurement gas on the condensation areas, according to DE 200 12 060 U1 said areas have a hydrophilic surface, whereas the remaining areas are hydrophobic.

U.S. Pat. No. 3,528,278 discloses another dew point sensor in which the light is passed through a light guide and on its surface is reflected in condensation-dependent manner back into the light guide.

DE 100 56 771 C2 proposes the provision on the sensitive surface of dew point humidity sensors of periodically arranged, hydrophilic surfaces, which are surrounded by hydrophobic areas. The hydrophilic surfaces can in particular be used to bring about a start of the condensation process before the dew point temperature is reached. The hydrophilic areas are wetted and with increasing condensation time droplets with a relatively steep wetting angle can be formed. In the case of sensors designed in this way, in certain circumstances comparatively long condensation times can arise and the sensors then react comparatively slowly.

DE 35 43 155 C2 discloses an optical dew point sensor with an optical waveguide having a roughening on its surface. If this roughening is unwetted, a considerable proportion of the light coupled or fed into the optical waveguide passes out through the roughening. However, if on dropping below the dew point the roughened area is wetted, the light intensity loss there is lower.

Another optical dew point hygrometer is known from EP 0 843 174 A1. This known dew point hydrometer detects a condensate coating which forms on a cooled, curved optical fibre.

U.S. Pat. No. 5,396,325 discloses another optical sensor permitting the detection of the formation of water droplets on a measurement surface on the basis of a change to the surface reflectivity.

The article by Lance D. Eske, David W. Galipeau "Characterization of SiO.sub.2 surface treatments using AFM, contact angles and a novel dew point technique", published in Colloids and Surfaces A, 154 (1999), pp 33-51 describes the use of surface acoustic wave (SAW) sensors for detecting the bedewing of a surface.

Another dew point mirror hygrometer is described in the article "The measurement of tiny dew droplets at the initial deposition stage and dew point using a phase-shift interference microscope" by Shigeaki Matsumoto, published in the journal "Measurement Science and Technology", 14 (2003), pp 2075-2080.

BRIEF SUMMARY OF THE INVENTION

The object of the invention is to provide a device for determining the dew point temperature of a measurement gas having a particularly high measurement accuracy and which in particular can be economically manufactured in large numbers.

According to a first aspect of the invention the condensation surface has a semihydrophobic construction.

This first aspect is based on the finding that, on dropping below the dew point temperature on a known, hydrophilic condensation surface, a substantially smooth water film of limited thickness is formed and its surface at the transition to the measurement gas is approximately parallel to the condensation surface. However, at said parallel water film surface light passing out of the light guide is reflected and possibly even totally reflected and coupled back into the light guide on the light sensor. As a result of this coupling or feeding back of light into the light guide the proportion of light coupled or fed out during the bedewing of the condensation surface is reduced and consequently the precision, particularly the signal-to-noise ratio of the device is decreased.

However, in the case of the semihydrophobic condensation surface according to the invention in general no smooth water film is formed and instead there are numerous small droplets which, as a result of their geometry, lead to the deflection of the light. In particular, there is no coupling back into the light guide and/or light sensor of the light coupled out into the droplets on the condensation surface, so that the accuracy of the device according to the invention is increased compared with the prior art.

Besides its use for dew point determination, the inventive device can also be used for determining the frost point. On reaching the frost point ice crystals form on the semihydrophobic condensation surface and also deflect light.

In experiments with semihydrophobic condensation surfaces it has been found that even droplets which form in the initial stage after dropping below the dew point and which are invisible to the naked eye, lead to a reliable light deflection as a result of their geometry. Thus, at the light sensor clear intensity decreases of the measurement signal are observed on bedewing. Even with a marked droplet growth after a bedewing period of roughly thirty minutes it was not possible to detect any film formation. Instead the bedewing droplets were uniformly distributed over the bedewed surface.

A semihydrophobic surface can in particular be understood to mean a surface where droplet formation starts at the commencement of condensation.

A semihydrophobic surface can e.g. be characterized in that on it, in air as the measurement gas, there is a contact angle with water exceeding 25.degree., 30.degree., 40.degree., 50.degree., 60.degree. or 70.degree. and which is smaller than 110.degree. or 90.degree. Therefore a semihydrophobic surface has surface characteristics, particularly surface energies, between those of hydrophobic and hydrophilic surfaces. The contact angle is appropriately not excessive, so that for the same droplet volume there is a large contact surface with the condensation surface and therefore a large light coupling in area to the light guide. In particular, the contact angle can be between 50.degree. and 90.degree. and/or be in preferred manner 40.degree.+−0.50, 45.+−0.10.degree. or 80.degree.+−0.5.degree.

According to the invention it is particularly advantageous that the condensation surface is semihydrophobic throughout, particularly with a roughly constant contact angle to a condensing phase of the measurement gas. The condensing phase can in particular be water and the measurement gas air. According to this embodiment the condensation surface has over its entire extent at least approximately identical surface characteristics, particularly surface energies. This permits a particularly good uniformity of the bedewing droplets and therefore a particularly precise determination of the dew point temperature.

It is also advantageous that the contact angle of the semihydrophobic condensation surface to the condensing phase of the measurement gas exceeds 30.degree. and preferably exceeds 40.degree., 50.degree. or 60.degree. It is also advantageous for the contact angle of the semihydrophobic condensation surface to the condensing phase of the measurement gas to be smaller than 110.degree. and preferably smaller than 90.degree.

According to the invention it is particularly preferred that the light guide, particularly in the vicinity of the condensation surface, has glass, a semiconductor material, e.g. silicon, and/or a plastics material, e.g. polycarbonate. The light guide can also be referred to as the substrate. The glass can in particular be quartz glass or borosilicate float glass or borofloat glass. The light guide can e.g. also have crystalline quartz, sapphire or diamond. Advantageously the condensation surface is formed directly on the light guide surface. However, it is also possible to provide on the light guide surface a further material layer on which in turn is formed the condensation surface. The light guide is preferably made from the same material throughout.

The condensation surface can be constructed with a comparatively high surface roughness. For this purpose the condensation surface can be roughened in planned manner, as described in DE 35 43 155 C2. However, in the case of a roughened condensation surface in certain circumstances dirt particles can give rise to a smoothing of the condensation surface in the same way as condensate and can consequently simulate wetting. A particularly contamination-insensitive device can consequently be obtained if the condensation surface is smooth. It is particularly preferred that the mean roughness (Ra) of the condensation surface is below 100 nm, particularly below 10 nm or 2 nm. Advantageously the roughness is approximately 0.5 to 0.7 nm. Appropriately the mean roughness is approximately identical over the entire condensation surface, so that a particularly uniform droplet distribution can be obtained.

In order to keep low the heat flow in the light guide between the condensation surface area and the remaining light guide and therefore also keep low the energy requirements of the means for adjusting. the condensation surface temperature, it is advantageous for the specific thermal conductivity of the light guide to be comparatively low, at least in the area round the condensation surface, i.e. the light guide is a comparatively poor heat conductor. This leads to a limited heat dissipation to connections, terminals and/or a housing of the device. With a low specific thermal conductivity of the light guide in the area round the temperature-controlled condensation surface significant temperature gradients can occur, so that it can be ensured that there is a dewing only in the vicinity of the condensation surface, but not in the surrounding surface areas. Through the choice of a low specific thermal conductivity of the light guide it is also possible to largely prevent an extraneous coupling in of heat.

However, in the vicinity of the condensation surface a good thermal conductivity is advantageous in order to bring to the condensation surface the thermal energy of the means for adjusting its temperature with a temperature gradient as low as possible. However, the surrounding area is preferably a poor heat conductor in order to thermally disconnect the condensation area from the housing. To obtain a good heat coupling to the temperature adjustment means and simultaneously a poor heat coupling to the housing, particularly with an integral light guide construction it is advantageous for it to be particularly thin in the condensation area, especially compared with the area round the condensation area.

In order to obtain a low specific thermal conductivity, the light guide can in particular be made from glass. In particularly preferred manner the specific thermal conductivity of the light guide, at least in the area round the condensation surface, is lower than 10 W/(K.times.m), particularly lower than 1 W/(K.times.m). In order to bring about a good temperature control of the condensation surface with low light guide specific thermal conductivities, appropriately there is a good thermal coupling or contact of the temperature adjustment means of the condensation surface with the light guide. For this purpose said means, which are e.g. in Peltier element form, are advantageously joined to the light guide by a heat conducting paste layer.

To produce the semihydrophobic surface characteristics in the vicinity of the condensation surface the light guide can e.g. be chemically functionalized. Through an appropriate chemical functionalization the condensation surface can be sensitized specifically for the detection of certain substances. However, it is particularly preferred for the condensation surface to be a finished polished substrate surface. This is understood to mean that the surface of the light guide, i.e. the substrate, at least in the vicinity of the condensation surface, following polishing and optionally subsequent cleaning has not undergone and/or need not undergo any further surface-modifying processes.

At least in the vicinity of the condensation surface, the optical waveguide can also e.g. have SiC, SiON.sub.x and/or NiCr and can in particular be coated therewith.

It is fundamentally possible to space the light source and/or light sensor from the light guide. It is also possible to provide further coupling light guides, which are placed between the light source and light guide and/or between the light sensor and light guide. To keep contamination influences limited, preferably the light path from light source to light sensor essentially passes through a medium differing from the measurement gas.

However, according to a further independent aspect of the invention the light source and/or light sensor are located on the light guide, particularly on a back surface remote from the condensation surface. To this end the light source and/or light sensor can e.g. be bonded and/or melted onto the light guide. For adjusting the optical path it is also possible for the light source and/or light sensor to be displaceably located on the light guide. Advantageously a diaphragm is positioned between the light source and light guide and between the light sensor and light guide. If such diaphragms are provided, they can e.g. be vapour deposited, sputtered, printed, deposited, coated or bonded onto the light guide and in turn the light source and/or light sensor can be bonded onto the diaphragms. The diaphragms are appropriately placed on the light guide surface.

It is possible to couple or feed light into or out of the light guide with the condensation surface via further coupling light guides. These coupling light guides can be arranged at an angle to the condensation surface. By placing the light source and/or light sensor directly on the light guide, whilst interposing diaphragms, it is possible to manufacture the device in a particularly inexpensive, small dimensional form.

Through placing a diaphragm between light source and light guide, it is in particular possible to use a segment of the spatial intensity distribution of the light source for illuminating the condensation surface. The light source is preferably constructed at least approximately as a Lambertian emitter. Light which does not enter the light guide under the desired incidence angle .alpha. to the condensation surface, can be particularly easily and effectively cut out by the diaphragm. The diaphragm is advantageously reflecting, i.e. as silvering. Through the placing of the light source on the back surface of the light guide and the interposing of a diaphragm, without further coupling light guides being provided, the device according to the invention can have a particularly simple optical design.

In the coupling out area the diaphragm can prevent unwanted light from penetrating the light sensor, where it could lead to an overloading of the latter. Light diverging from the incidence angle, i.e. light under a different angle, is reflected at the diaphragms.

It is particularly preferred according to the invention for the light source to have a light emitting diode (LED) and/or the light sensor a photodiode. Through the use of such light emitting diodes and/or photodiodes it is possible to very economically manufacture particularly compact devices for dew point temperature determination.

According to the invention a particularly compact dew point temperature determination device can be obtained in that the means for adjusting the temperature are located on the back surface of the light guide remote from the condensation surface and/or, in the vicinity of the condensation surface and the temperature adjustment means, the light guide has a taper. The temperature adjustment means are advantageously in Peltier element form. Through the placing of the temperature adjustment means on the back surface of the light guide opposite to the condensation surface, a particularly good thermal coupling can be brought about between the means and the condensation surface, with at the same time a compact construction. Thermal coupling can be further improved by the formation of the taper in the light guide. A taper here is understood to mean an area of the light guide where the latter has a reduced thickness. The temperature adjustment means can in particular be located at the taper. Advantageously the light guide thickness at the taper, i.e. between the condensation surface and the temperature adjustment means, is roughly 1 mm or less.

According to the invention, for increasing the signal-to-noise ratio, the light guide and light source are constructed for multiple internal light reflection in the light guide, particularly in the vicinity of the condensation surface and/or the taper. To obtain a large number of internal reflections, the light guide thickness in the vicinity of the taper is advantageously as small as possible. To improve the reflectivity, the light guide can be coated, particularly silvered in surface areas spaced from the condensation surface and in particular on the back surface remote from the said condensation surface.

A particularly reliable dew point temperature determination device can inventively be obtained in that with the light source it is possible to generate a light bundle or beam in the optical waveguide, whose incidence angle on the condensation surface is between the critical angle of the light guide-measurement gas transition and the critical angle of the light guide-condensing phase transition. The term critical angle is here understood to mean the critical angle of the total reflection measured against the surface normal, i.e. the maximum incidence angle above which a light transition into the optically thinner medium is no longer possible and the light is virtually completely reflected. The light guide-measurement gas transition is understood to mean the transition between the optically thicker light guide and the optically thinner measurement gas. The light guide-condensing phase transition is to be understood in an analogue way.

As a result of the incidence angle between the two indicated critical angles provided according to the invention, in the case of an unbedewed condensation surface the light is totally reflected by the latter. If there are water droplets on the condensation surface the light is at least partly coupled out of the light guide into the water droplets and from there into the surrounding measurement gas. This leads to an attenuation of the light intensity in the light sensor in the case of condensation surface bedewing, which can serve as a measure for the reaching of the dew point temperature on the condensation surface. The measurement gas can in particular be air and the condensing phase in particular water. In this case the critical angle of the light guide-measurement gas transition is e.g. approximately 40.degree. and the critical angle of the light guide-condensing phase transition is e.g. approximately 60.degree. These critical angles can in particular occur if the light guide is made from glass. In the case of light irradiation with the indicated incidence angle between the two critical angles, said incidence angle when the condensation surface is dry is above the current critical angle for the total reflection and when the condensation surface is bedewed it is below the current critical angle of the total reflection. Thus, a total reflection only occurs when the condensation surface is dry.

Besides water, the inventive device is also suitable for detecting other substances and materials, particularly with corresponding critical angles, and said other substances or materials then form the condensing phase. Through a suitable hydrophobing, i.e. by an appropriate choice of the surface energies of the condensation surface, the substances to be detected form droplets, which couple out the radiation under virtually all refractive indices.

According to the invention, for determining the condensation surface temperature a temperature-dependent conductor can be applied, particularly sputtered, to the light guide, particularly in the vicinity of the condensation surface. The temperature-dependent conductor can e.g. have aluminium, platinum and/or nickel. Appropriately the temperature-dependent conductor is placed round the condensation surface on the light guide surface. The temperature-dependent conductor can in particular be in the form of a metal coating.

If use is made of a semiconductor material, e.g. silicon, for the light guide, the inventive device can be constructed as part of an integrated circuit and e.g. have at least one p-n junction on the light guide. In particular, it is also possible to integrate the transmit/emit LED and/or the detector, i.e. the light sensor, which further decreases manufacturing costs.

The condensation surface is appropriately rectangular, especially square, but can also be circular. The circumference of the condensation surface preferably corresponds to the shape of the temperature adjustment means. The condensation surface is more particularly designed for a uniform temperature distribution. The external dimensions of the condensation surface are advantageously less than 5 mm. In particular, the external dimensions of the condensation surface can be 2.times.2 mm. The temperature-dependent conductor, which can also be called a temperature sensor, advantageously has a coating height of 100 to 200 nm and a coating width of less than 100.mu.m.

For the electrical insulation of the temperature-dependent conductor, particularly with respect to the measurement gas and/or condensing phase, an insulating passivating layer is appropriately provided on said conductor. This passivating layer can e.g. have $SiO_2$ and/or SiC and a layer thickness of approximately 1.mu.m. Through the use of SiC, i.e. silicon carbonate, it is possible to obtain particularly dense and/or non-porous passivating layers. The passivating layer can also extend onto the condensation surface.

According to the invention, the light can be NIR, IR, VIS and/or UV light, preference being given to NIR light.

The device according to the invention appropriately has a control and evaluating device, which is in signal connection, particularly line connection with the light source, light sensor, temperature-dependent conductor and the temperature adjustment means of the condensation surface. Through said control and evaluating device the condensation surface temperature can be controlled through the temperature adjustment means. The control and evaluating device can evaluate a change to the light intensity at the light sensor. With a constant light output of the light source such a light intensity change indicates a change to the bedewing state of the condensation surface and therefore to the fact that the dew point temperature is reached. The condensation surface temperature can be determined using the temperature-dependent conductor.

For compensating intensity fluctuations of the light source and which can in particular be due to light source ageing phenomena, it is advantageous according to the invention to provide in addition to the light sensor a reference light sensor for determining the light intensity of the light source. Advantageously the light from the light source to the reference light sensor passes through the light guide. In particular, the reference light sensor can be located on the light guide. To obtain a reliable reference signal at the reference light sensor, advantageously the light from the light source to the reference light sensor is kept spaced from the condensation surface.

A particularly compact arrangement of the reference light sensor relative to the light source and therefore a particularly compact device can be obtained in that on the light guide is provided a silvered area for reflecting the light source light to the reference light sensor. Advantageously the light source and/or reference light sensor are positioned on the back surface of the light guide remote from the condensation surface, whereas the silvered area is located on the front surface of the light guide on which also the condensation area is located.

According to the invention the light guide can also have a light coupling out area by means of which light emanating from the light source can be coupled out of the light guide, particularly for data transmission purposes. The light source appropriately generates transmit or emit signals, which can be coupled out into an optical system via the light coupling out area. The transmit signals can e.g. contain information concerning the dew point temperature and/or the state of the device. The light coupling out area can in particular be constructed as a scatter grid or as a roughening on the light guide surface. Such a scatter grid can have in cross-section triangular protuberances and/or depressions. To obtain a particularly reliable coupling out of light at the light coupling out area, it is advantageous for the latter to be thermally disconnected from the condensation surface. The light coupling out area can in particular be located on the front surface of the light guide. Apart from a light coupling out area, the light guide can also have a coupling in area, particularly a coupling in grid, by means of which optical transmit signals can be coupled into the light guide for information transmission purposes. The transmit or emit signals are advantageously IR transmit or emit signals.

BRIEF DESCRIPTION OF THE SEVERAL VIEWS OF THE DRAWINGS

The invention is described in greater detail hereinafter relative to preferred embodiments and the attached diagrammatic drawings, wherein show.

In all the drawings identically acting elements carry the same reference numerals.

DETAILED DESCRIPTION OF THE INVENTION

Figure 1:
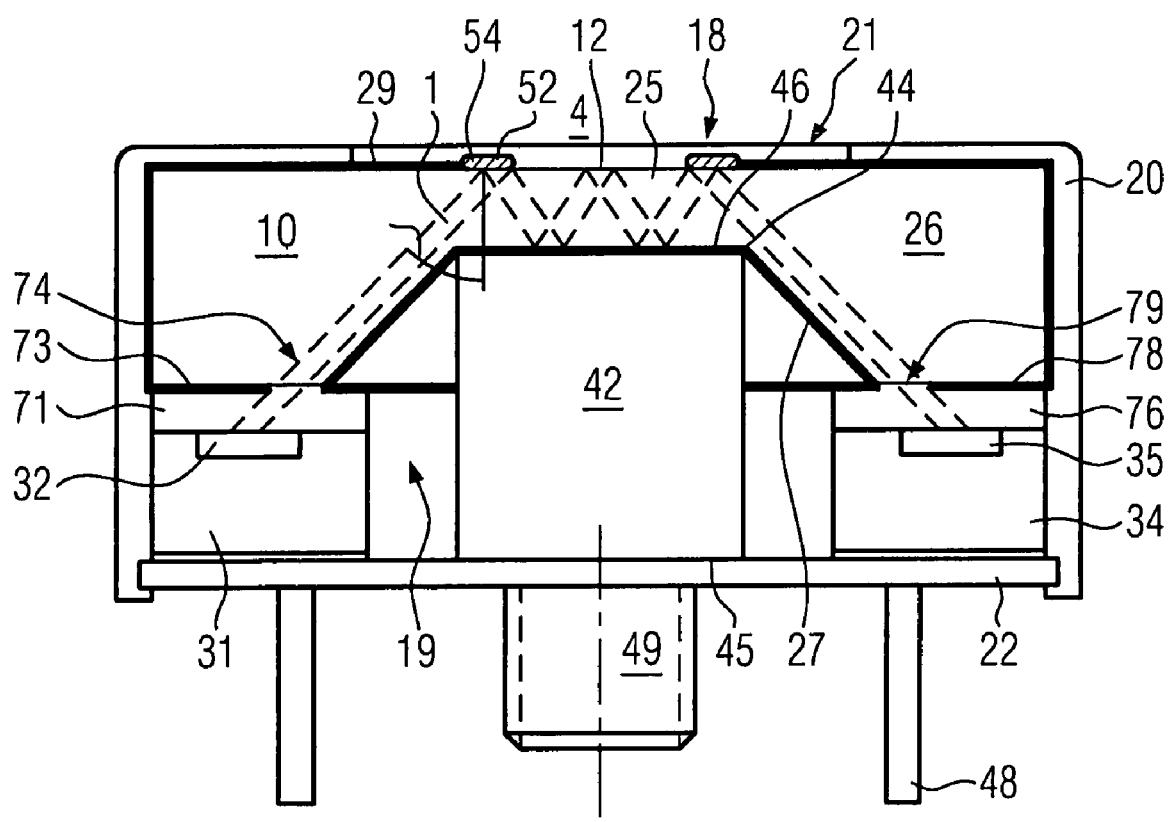
FIG. 1 A cross-sectional view of an inventive device for determining the dew point temperature in a first embodiment.

A first embodiment of an inventive device is shown in FIG. 1. The device has a light guide 10 constructed as a glass substrate and which can also be called a transparent body. A light source 31 in the form of a light emitting diode (LED) is located on the back surface 19 of light guide 10.

This light source 31 has an emit chip 32 for emitting light in the near infrared range (NIR). In said spectral range, the light guide 10, which can in particular be made from glass or plastic, is transparent. Between the light source 31 constructed as a LED and the light guide 10 are provided an adhesion promoting, transparent immersion coating 71 and a light-reflecting layer 73. The reflecting layer 73 is vapour-deposited on the light guide 10. It has a recess 74 forming a diaphragm through which light emission of light source 31 passes into light guide 10 in the form of a light bundle or beam 1. The recess 74 can e.g. be elongated, circular, oval, rectangular or square.

The light guide 10 is provided in a central area of its front surface 18 with a condensation surface 12, whose bedewing can be detected using the device according to the invention. On the back surface 19 of light guide 10 are provided means 42 for adjusting the temperature of the condensation surface 12 in the form of a Peltier element. For a particularly good thermal coupling of the condensation surface 12 to the temperature adjustment means 42, the latter are placed by means of a heat-conducting layer 44, which can e.g. be in the form of a heat conducting paste, on light guide 10. The temperature adjustment means 42 can also be referred to as a heating and cooling element.

To further improve the thermal coupling of the condensation surface 12 with the temperature adjustment means 42, in the area between condensation surface 12 and said temperature adjustment means 42 the light guide is constructed with a taper 25, in the vicinity of which the thickness of the light guide 10 is reduced to approximately 1 mm. For forming the taper 25 between the latter and the outer areas 26 of light guide 10 sloping boundary surfaces 27 with respect to the front surface 18 of light guide 10 are provided on the back surface 19 of light guide 10. However, in the embodiment shown the front surface 18 of light guide 10 is planar throughout, but can e.g. also be domed.

Tests have shown that the uniformity of the bedewing of the condensation surface 12 is dependent on the heat transfer resistance between the temperature adjustment means 42 and the light guide 10 and that the uniformity can in particular be improved by a good, uniform thermal coupling between said two elements.

For determining the temperature of the condensation surface 12, in the vicinity of the latter a temperature-dependent conductor 52 in the form of a temperature-dependent layer is applied directly to light guide 10. The temperature of the condensation surface 12 can be determined with a low heat conduction coefficient using said temperature-dependent conductor 52 which, in plan view, virtually completely embraces condensation surface 12. In particular, if the light conductor 10 is made from a low thermal conductivity and low thermal capacity material, it is advantageous that the temperature-dependent conductor 52 used extracts a minimum of thermal energy from condensation surface 12.

The recess 74 in reflection layer 73 is positioned in such a way that the light bundle 1 passing out of light source 31 into light guide 10 strikes the condensation surface 12 in light guide 10 under an incidence angle .alpha. which is between the critical angle $\alpha_{G,LM}$ the light guide-measuring gas transition and the critical angle $\alpha_{G,LK}$ of the light guide-condensing phase transition. This is explained in greater detail relative to FIG. 5.

As a result of the selected incidence angle .alpha., in the case of a dry condensation surface 12, light bundle 1 is totally reflected on said surface 12. From here the reflected light bundle 1 impinges on the back surface 19 of light guide 10 which is provided with a reflecting coating 46 at least in the vicinity of the temperature adjustment means 42 in order to improve light reflection. Thus, the light bundle 1 is also reflected on the back surface 19 of light guide 10 and from there again impinges on condensation surface 12 under incidence angle .alpha. and is reflected again. Thus, in the vicinity of taper 25 there is a multiple reflection of light bundle 1, the number of reflections increasing with decreasing material thickness of taper 25. The measuring effect of the inventive device can be increased by raising the number of reflections.

Following a final reflection on condensation surface 12, the light bundle 1 passes through a further diaphragm-forming recess 79 in another reflecting layer 78 and through a further immersion layer 76 onto a sensitive layer 35 of a light sensor 34 also located on the back surface 19 of light guide 10.

Figure 5:
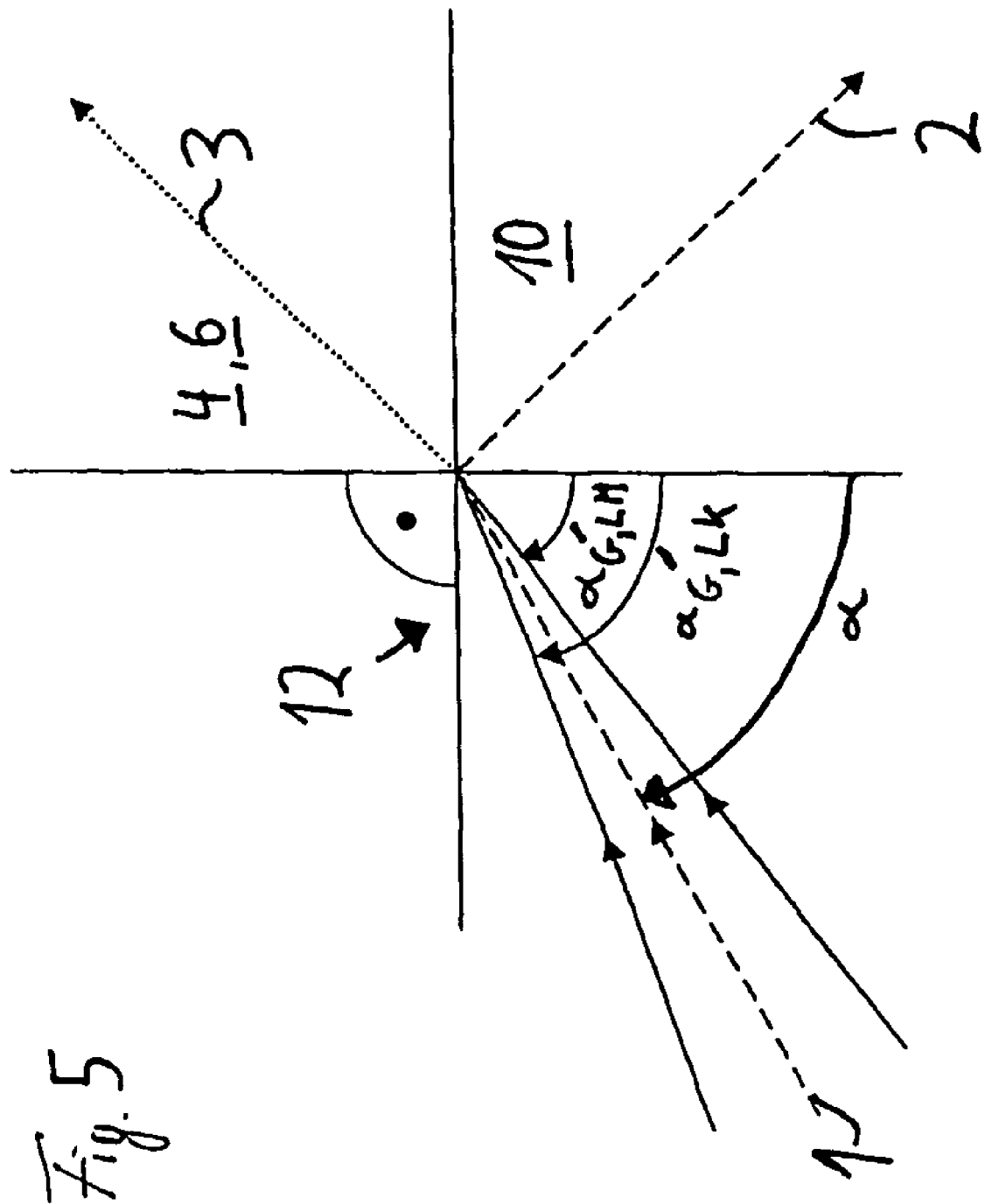
FIG. 5 The optical path on a condensation surface.
Figure 6:
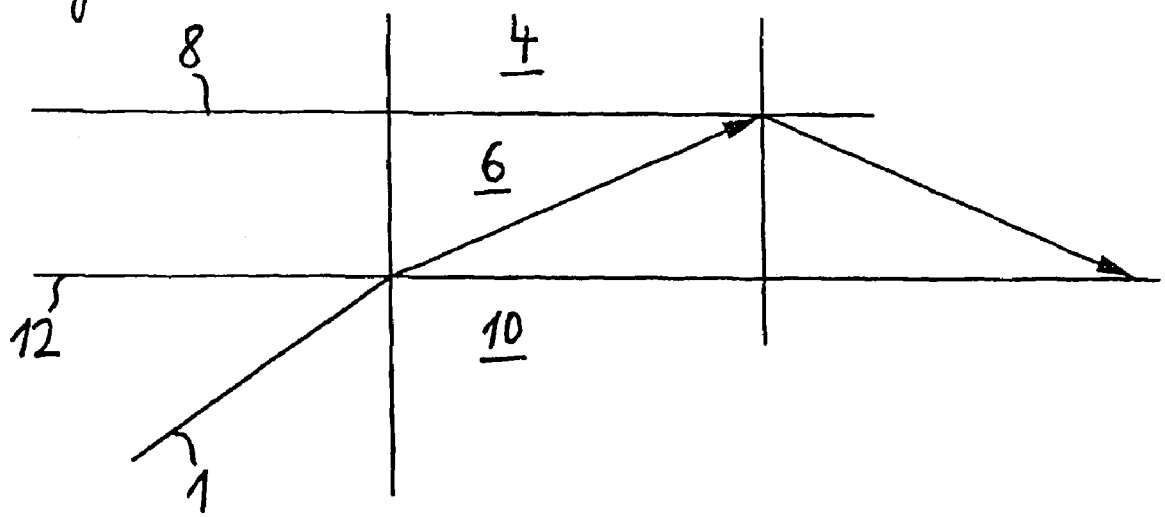
FIG. 6 The optical path on a bedewed condensation surface with hydrophilic characteristics.
Figure 7:
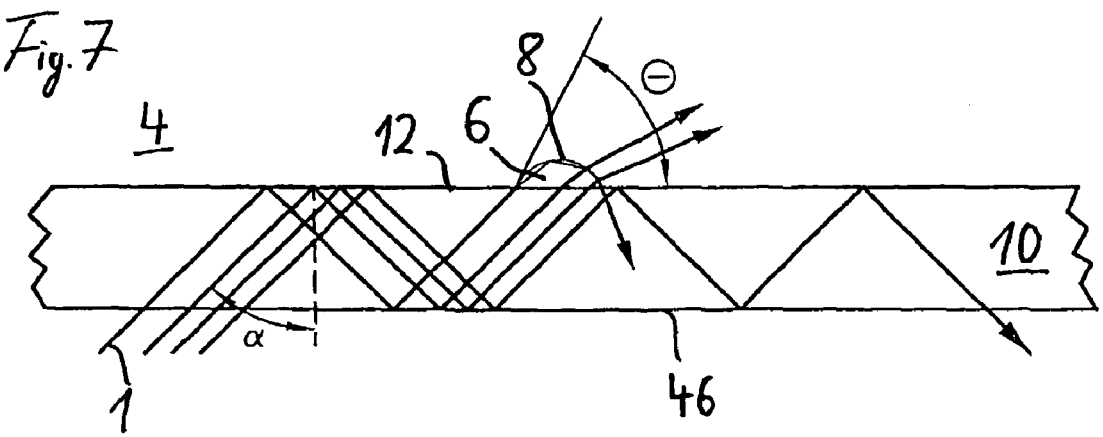
FIG. 7 The optical path on a bedewed condensation surface with semihydrophobic characteristics.

If as a result of a reduction in the temperature of the condensation surface 12 bedewing occurs thereto, in the manner explained in greater detail relative to FIGS. 5 to 7, the light bundle 1 is no longer completely reflected on condensation surface 12 and is instead at least partly coupled out into the surrounding measurement gas 4. Due to this incomplete reflection there is a reduction of the light intensity at light sensor 34. Therefore a reduction in the light intensity at light sensor 34 can be used as an indication of bedewing of the condensation surface 12. According to the invention the condensation surface 12 on light conductor 10 faces light source 31 and light sensor 34.

The boundary surfaces 27 also provided with reflecting layer 46 run roughly parallel to light bundle 1, i.e. under incidence angle .alpha. to the normal of the front surface 18. As a result it can be ensured that stray light, which impinges under an undesired angle differing from incidence angle .alpha. is reflected by said boundary surfaces 27 and does not reach light sensor 34.

For electrically insulating the temperature-dependent conductor 52 relative to the measurement gas 4, a passivating layer 54 of SiC or $SiO_2$ is applied to said conductor 52.

The device shown in FIG. 1 has a housing 20, which houses light guide 10, light source 31, light sensor 34 and the means 42 for adjusting the temperature of condensation surface 12. In the vicinity of condensation surface 12 housing 20 is provided with an opening 21 to ensure the interaction of measurement gas 4 with condensation surface 12. Opening 21 is chosen with an appropriate size for there to be a minimum thermal contact which is normally produced by housing 20 with condensation surface 12. Through the choice of a large spacing between condensation surface 12 and housing 20 the temperature distribution in the vicinity of condensation surface 12 can be kept largely uniform. The temperature distribution uniformity can be further improved by keeping low the thermal conductivity of light guide 10.

In the area between housing 20 and condensation surface 12 the front surface 18 of light guide 10 is also provided with a reflecting layer 29 to reduce stray light influences. Appropriately reflecting layers 46, 73, 78 and/or 29 are connected.

The housing 20 is provided on its back surface with a bottom 22 to which are coupled the means 42 for adjusting the temperature of condensation surface 12 using a further heat-conducting layer 45, preferably of heat conducting paste. A threaded pin 49 for fixing a heat dissipation adaptor not shown in FIG. 1 is provided on bottom 22 and/or on temperature adjustment means 42.

For contacting light source 31, light sensor 34, temperature adjustment means 42 and temperature-dependent conductor 52 electric contact pins 48 are provided on bottom 22 of housing 20.

Figure 2:
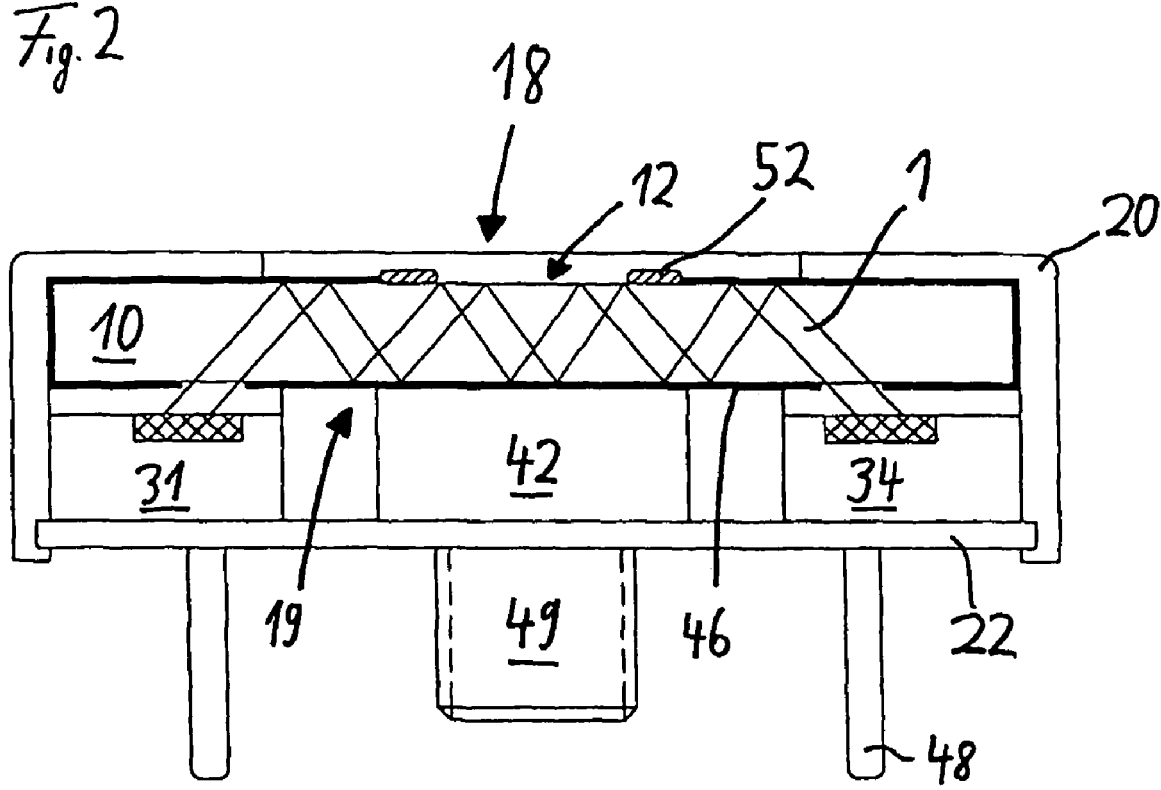
FIG. 2 A cross-sectional view of an inventive device in a second embodiment.

Another embodiment of a device according to the invention is shown in FIG. 2. This embodiment essentially differs from that of FIG. 1 in that in the vicinity of condensation surface 12 there is no taper 25. Instead the material thickness of light guide 10 is essentially constant over its entirety. In the case of the device shown in FIG. 2 there are consequently no sloping boundary surfaces 27.

Figure 3:
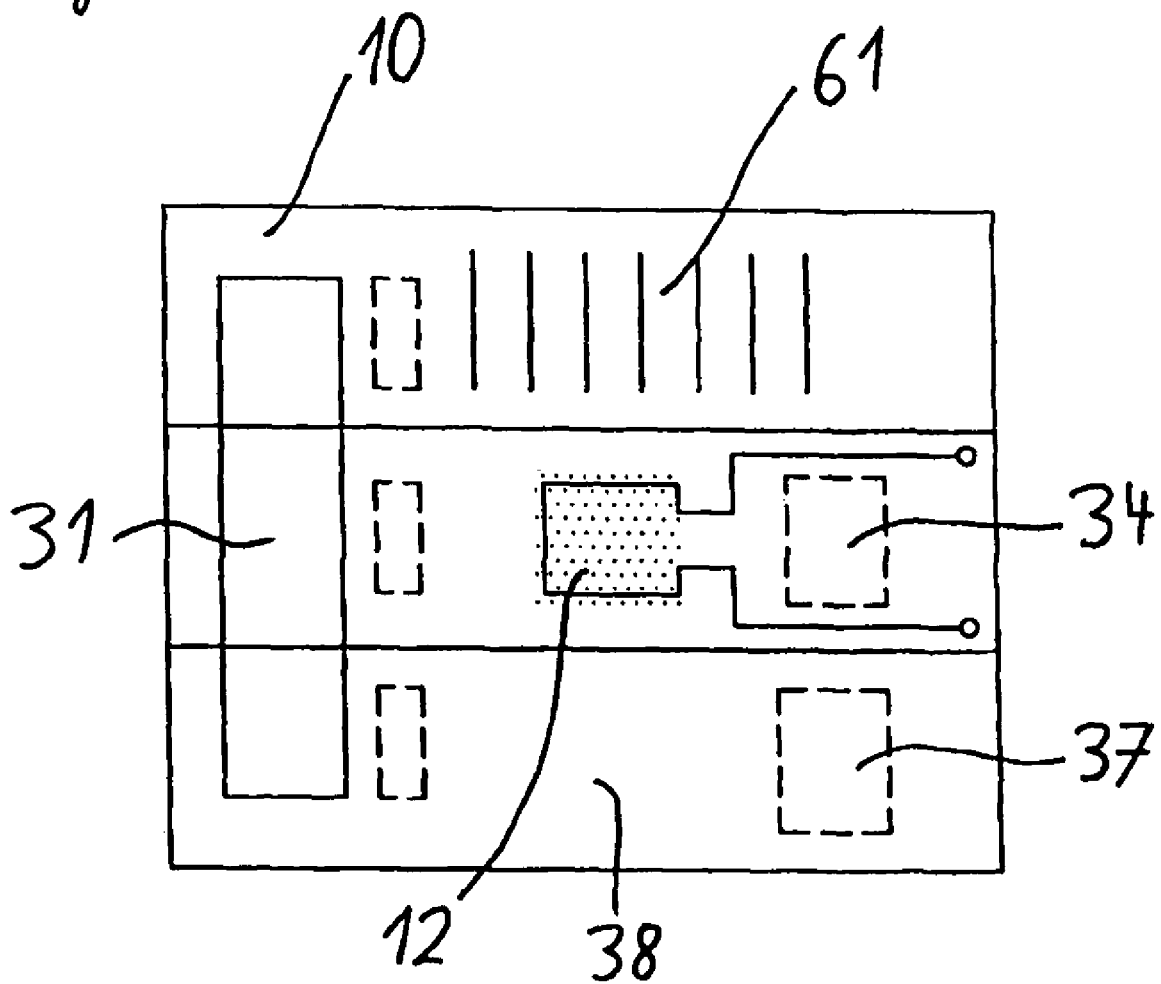
FIG. 3 A plan view of an inventive device in a further embodiment.
Figure 4:
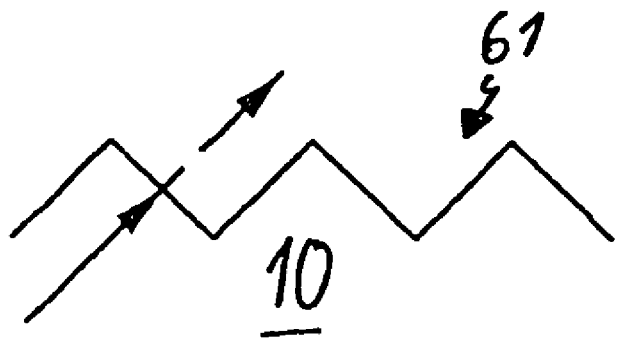
FIG. 4 A detail cross-sectional view of the light coupling out area of FIG. 3.

A further embodiment of an inventive device 4 is shown in FIGS. 3 and 4. This device has in light guide 10 a reference path making it possible to detect ageing and an associated intensity decrease of light source 31. For this purpose on light guide 10 there is a silvered area 38 through which part of the intensity of light source 31 is fed into a reference light sensor 37. On evaluating the signal of light sensor 34, the signal of reference light sensor 37 can be taken into account for compensating the intensity decrease of light source 31.

The embodiment of FIG. 3 also has a light coupling out area 61 for the planned, bedewing-independent coupling out of part of the light intensity of light source 31. By means of said light coupling out area 61 it is possible to couple out of the device information on the state thereof modulated on the intensity of light source 31. As shown in FIG. 4, the light coupling out area 61 is formed by a grid with triangular and/or pyramidal protuberances and depressions on the surface of light guide 10. It can also be formed by a roughening.

FIG. 5 shows the path of a light bundle 1, shown as a light beam, on an inventive condensation surface 12, when the latter is in the dry and the bedewed state. According to the invention the light bundle 1 impinges on condensation surface 12 under an incidence angle $\alpha$ between the critical angle for total reflection $\alpha_{G,LM}$ of the light guide-measuring gas transition and the critical angle for total reflection $\alpha_{G,LK}$ of the light guide-condensing phase transition.

Thus, if condensation surface 12 is dry, i.e. the measurement gas 4 is adjacent to light guide 10, the incidence angle $\alpha$ of light bundle 1 is larger than the present critical angle $\alpha_{G,LM}$. Therefore, as indicated by light bundle 2, light bundle 1 is totally reflected on the condensation surface.

However, if the condensation surface 12 is bedewed, i.e. the condensing phase 6 is adjacent to light guide 10, then the incidence angle $\alpha$ is smaller than the present critical angle $\alpha_{G,LK}$. Thus there is only a partial reflection on condensation surface 12 and part of the light intensity of light bundle 1 is coupled in light bundle 3 from light guide 10 into condensing phase 6.

The optical path on a bedewed, hydrophilic condensation surface 12 is shown in FIG. 6. Due to the hydrophilic properties of condensation surface 12, the condensing phase 6 constituted by water forms an extended water film on light guide 10. At the transition between the water film and the measurement gas 4 an interface 8 is formed, which runs substantially parallel to condensation surface 12. On said interface 8 the light bundle 1 coupled out of light guide 10 is reflected and coupled back into light guide 10. As a result of this coupling back the proportion of light coupled out of light conductor 10 in the case of bedewing is reduced and therefore the change to the light intensity at light sensor 34 in the case of bedewing is decreased.

A light guide 10 with an inventive semihydrophobic condensation surface 12 is shown in FIG. 7. Due to the semihydrophobic properties of condensation surface 12, the condensing water phase 6 does not form on said surface a continuous water film and is instead deposited in the form of individual droplets with a contact angle $\Theta$ of approximately 90.degree. Therefore the interface 8 between the condensing water phase 6 and the measurement gas 4, with the exception of the top spots of the droplets, does not run parallel to condensation surface 12, as would be the case with a hydrophilic surface. As a result of this non-parallel path of interface 8, part of the light coupled out of light guide 10 into condensing phase 6 is coupled from the latter directly into the surrounding measurement gas 4 and is in particular not coupled back into light guide 10. The remaining part of the light coupled out into condensing phase 6 and which is then coupled back into light guide 10 is coupled back with a changed incidence angle due to the lack of parallelism between interface 8 and condensation surface 12 and is consequently largely also not detected by light sensor 34. The light intensity coupled out into condensing phase 6 from light guide 10 therefore contributes at best insignificantly to the intensity at light sensor 34.

Figure 8:
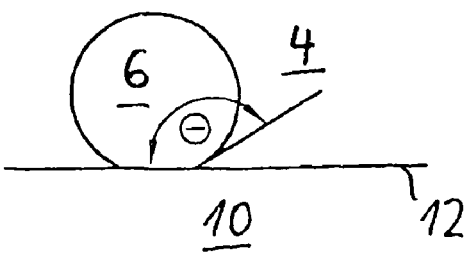
FIG. 8 A cross-sectional view of a condensate droplet on a hydrophobic condensation surface.

FIG. 8 shows a water droplet on a hydrophobic condensation surface 12. As can be gathered from FIG. 8, due to the large contact angle $\Theta$, only a small part of the condensing water phase 6 contributes to the wetting of condensation surface 12 and therefore to the coupling out of light. Therefore, with a hydrophobic condensation surface 12, the change to the light intensity in light sensor 34 in the case of bedewing is comparatively limited.

The invention claimed is:

1. A device for determining the dew point temperature of a measurement gas, the device comprising:
   a light guide,
   a semihydrophobic condensation surface, whose reflectivity is dependent on the condensation of the measurement gas, located on the light guide,
   a light source for emitting light through the light guide onto the condensation surface,
   a light sensor for determining the light intensity reflected back into the light guide by the condensation surface
   means for adjusting the temperature of the condensation surface, and at least one diaphragm provided on the light guide, between the light source and the light guide or between light guide and the light sensor.

2. The device according to claim 1, wherein the condensation surface is semihydrophobic throughout, with a roughly constant contact angle ($\Theta$) to a condensing phase of the measurement gas.

3. The device according to claim 1, wherein the contact angle ($\Theta$) of the semihydrophobic condensation surface to the condensing phase of the measurement gas is greater than 30°.

4. The device according to claim 1, wherein the contact angle ($\Theta$) of the semihydrophobic condensation surface to the condensing phase of the measurement gas is smaller than 110°.

5. The device according to claim 1, wherein in the area around the condensation surface, the light guide is glass, a semiconductor material, and/or a plastic material.

6. The device according to claim 1, wherein the mean roughness of the condensation surface is smaller than 100 nm.

7. The device according to claim 1, wherein the specific thermal conductivity of the light guide, at least in the vicinity of the condensation surface, is lower than 10 W/(K×m).

8. The device according to claim 1, wherein the condensation surface has a passivating layer made of SiC.

9. The device according to claim 1, further comprising a back surface on the light guide, wherein the light source and/or the light sensor are located on the light guide, on the back surface remote from the condensation surface.

10. The device according to claim 1, wherein the light source has a light emitting diode and/or the light sensor has a photodiode.

11. The device according to claim 1, wherein the temperature adjustment means are located on the back surface of the light guide remote from the condensation surface and in the vicinity of the condensation surface and the temperature adjustment means, the light guide having has a taper.

12. The device according to claim 1, wherein the light guide and the light source are constructed for multiple, internal light reflection in the light guide, particularly in the vicinity of the condensation surface and/or the taper.

13. The device according to claim 1, wherein the light source can generate a light bundle or a beam in the light guide, whose incidence angle ($\alpha$) on the condensation surface is between the critical angle ($\alpha_{G,LM}$) of the light guide-measuring gas transition and the critical angle ($\alpha_{G,LK}$) of the light guide-condensing phase transition.

14. The device according to claim 1, wherein a temperature-dependent conductor is applied by sputtering to the light guide, in the vicinity of the condensation surface.

15. The device according to claim 1, wherein the light is NIR, IR, VIS and/or UV light.

16. A device for determining the dew point temperature of a measurement gas, the device comprising:

a light guide;
a condensation surface, whose reflectivity is dependent on the condensation of a measurement gas, located on the light guide;
a light source for emitting light through the light guide onto the condensation surface;
a light sensor for determining the light intensity reflected back into the light guide by the condensation surface;
a reference light sensor for determining the light intensity of the light source; and means for adjusting the temperature of the condensation surface, wherein the condensation surface is semihydrophobic.

17. The device according to claim 16, wherein on the light guide is provided a silvered area is provided for reflecting the light of the light source to the reference light sensor.

18. The device according to claim 1, wherein on the light guide a light coupling out area is provided by means of which light emanating from the light source, for data transmission purposes, can be coupled out of the light guide.

19. The device according to claim 16, wherein on the light guide a light coupling out area is provided by means of which light emanating from the light source, for data transmission purposes, can be coupled out of the light guide.

* * * * *